United States Patent [19]

Boeckel et al.

[11] 4,423,699

[45] Jan. 3, 1984

[54] CENTRIFUGE ROTOR APPARATUS FOR PREPARING PARTICLE SPREADS

[75] Inventors: John W. Boeckel, Hamden; Vernon C. Rohde, Newtown, both of Conn.; John R. Wells, Los Angeles, Calif.

[73] Assignee: E. I. Du Pont de Nemours & Co., Wilmington, Del.

[21] Appl. No.: 15,911

[22] Filed: Feb. 28, 1979

[51] Int. Cl.³ .............................................. B05C 11/08
[52] U.S. Cl. ........................................ 118/52; 118/407
[58] Field of Search ..................... 118/52, 407, 412; 427/2, 240; 23/230 B; 264/317

[56] References Cited

U.S. PATENT DOCUMENTS

| | | | |
|---|---|---|---|
| 3,352,280 | 11/1967 | Hughes et al. | 118/319 X |
| 3,619,865 | 11/1971 | Hazzard | 118/52 X |
| 3,705,048 | 12/1972 | Staunton | 118/52 X |
| 3,906,890 | 9/1975 | Amos et al. | 118/52 X |
| 4,093,350 | 6/1978 | Fisli | 427/240 X |

FOREIGN PATENT DOCUMENTS 1553147  9/1979  United Kingdom .

OTHER PUBLICATIONS

Leif et al., "Centrifugal Cytology IV, The Preparation of Fixed Stained Dispersions of Gynecological Cells", *Acta Cytologica*, vol. 19, No. 2, Mar.-Apr. 1975, pp. 159-168.
"A Slide Centrifuge: An Apparatus for Concentrating Cells in Suspension onto a Microscope Slide", Watson, Reprinted from The Journal of Laboratory and Clinical Medicine, vol. 68, No. 3, pp. 494-501, Sep. 1966.
Dore et al., A Device for Preparing Cell Spreads, *Immunology*, Mar. 1965, vol. 9, pp. 403-405.
Dunlap et al., Centrifugal Cylology, *The Journal of Histochemistry and Cytochemistry*, vol. 23, No. 5, pp. 369-377, 1975.
Leemann et al., A Centrifugation Technique for Cytochemical Preparations, *The Journal of Histochemistry and Cytochemistry*, vol. 19, No. 12, 1971, pp. 758-760.
Ingram et al., Semiautomatic Preparation of Coverglass Blood Smears Using a Centrifugal Device, *The American Journal of Clinical Pathology*, vol. 51, No. 2, 1969, pp. 214-221.
Lee et al., Automated System for Fractionation of Blood Samples, *Clinical Chemistry*, vol. 24, No. 8, 1978, pp. 1361-1365.

*Primary Examiner*—John P. McIntosh

[57] ABSTRACT

A centrifuge rotor is described which facilitates the preparation of cell dispersions on microscope slides. The rotor is bowl-like in configuration and defines an annular channel having plural circumferentially disposed septa. The septa provide plural separate regions each adapted to receive removable chambers. The outer wall in each region is flat to accommodate a microscope slide. Each chamber has an outlet orifice adapted to contact the microscope slide. A sample containing blood cells, for example, may be placed in each chamber and the cells centrifugally sedimented against the slide associated with the respective chambers. A gasket at the interface between each slide and its chamber prevents leakage of the sample and a conduit in each chamber permits removal of the supernatant fluid following cell sedimentation.

11 Claims, 6 Drawing Figures

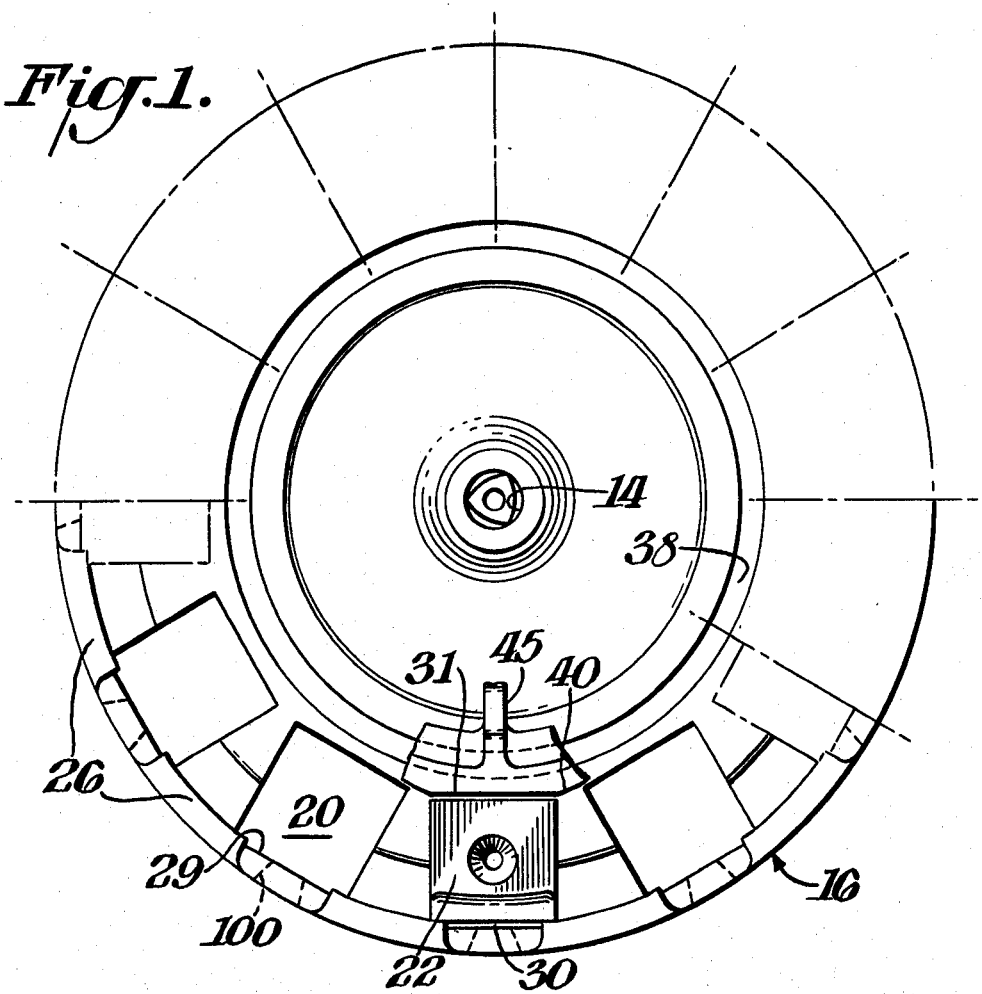
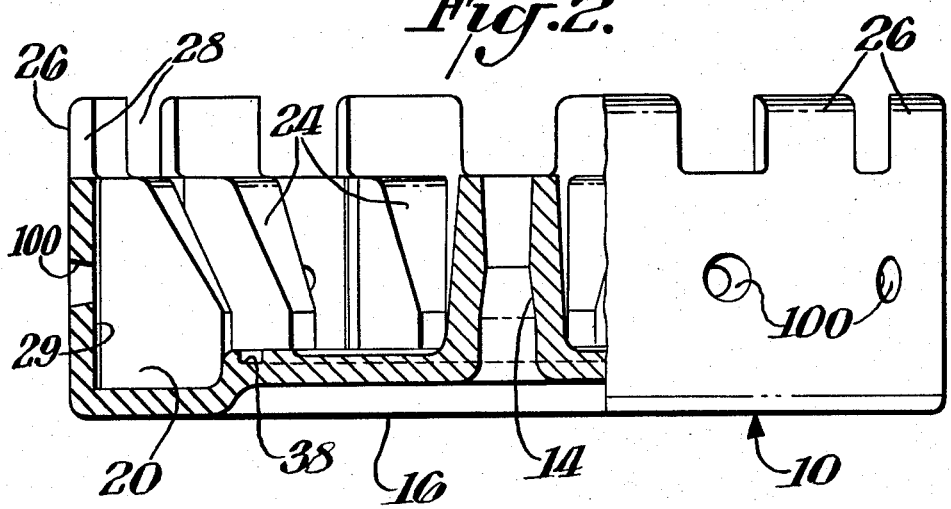

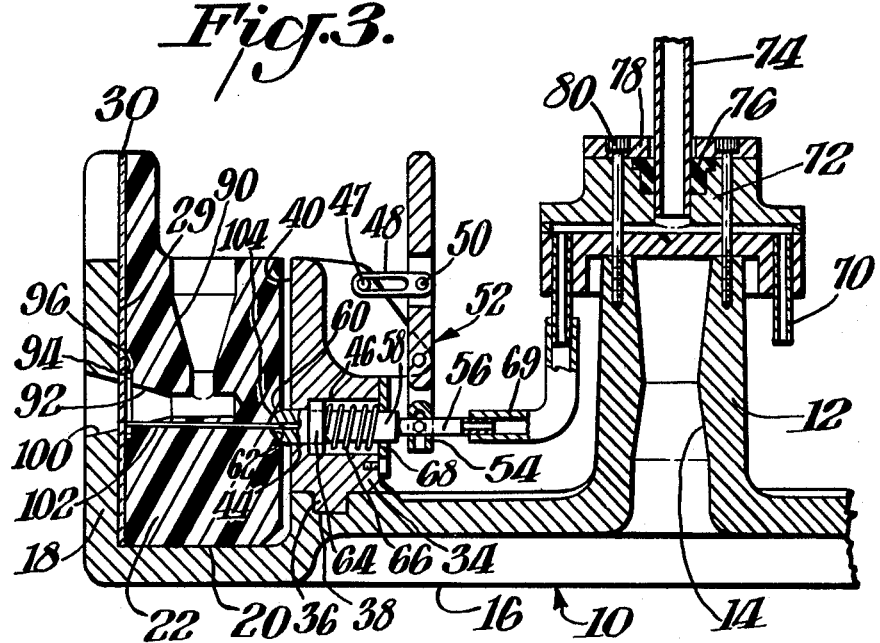
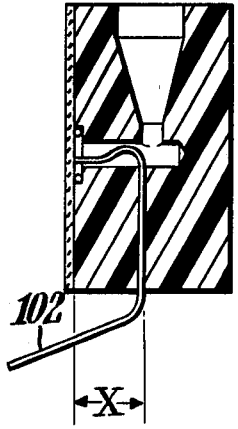
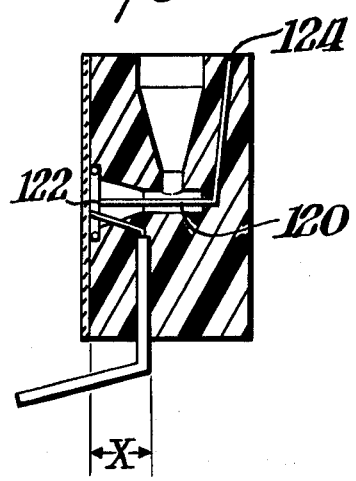
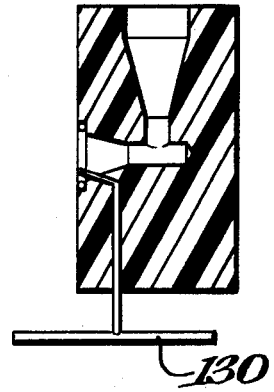

CENTRIFUGE ROTOR APPARATUS FOR PREPARING PARTICLE SPREADS

BACKGROUND OF THE INVENTION

This invention relates to centrifuge rotors and, more particularly, to a centrifuge rotor adapted to deposit sample particles on surfaces.

Various devices are known for depositing blood cells on microscope slides. Among these are those devices described in U.S. Pat. Nos. 3,705,048 and 3,906,890. These devices rotate a slide about an axis perpendicular to the slide itself such that blood deposited on the slide is driven by centrifugal force across the surface of the slide thereby widely distributing the blood cells of the sample. Such devices provide a relatively rapid, uniform technique for effecting blood counts and the like.

In other applications it is desirable to obtain a greater concentration of cells on the slide and to somewhat flatten the cells so that their structure may be ascertained. One device for this purpose is available and sold under the name "Cytospin" by Shandon-Elliott. Such device utilizes a bowl-type centrifuge rotor whose outer periphery defines a vertical wall adapted to receive microscope slides. Chambers for holding samples to be sedimented are positioned radially against the slides with a piece of filter paper between each chamber and its slide. A hole in the filter paper is positioned over an outlet orifice of the chamber such that cells in a fluid introduced into the chamber, when centrifuged, are driven against the slides. The filter paper serves the function of withdrawing excess fluid from the surface of the slide such that the sedimented cells can remain in position.

Unfortunately, the filter paper can have a deleterious effect. It tends to absorb the fluid so rapidly that the cells are literally "sucked" into the peripheral edges of the filter paper surrounding the outlet orifice with relatively few cells having sufficient time to pellet or sediment against the slide itself. For this reason the cells tend to run dry. It is more desirable to sediment the cells while they are wet since they tend to remain rounded if the applied centrifugal force doesn't exceed the osmotic pressure of the cell. Another problem encountered with the use of filter paper is that the sample volume that can be used is relatively small. For this reason only the cells of a single sample can be deposited on a given slide. The buildup of cells by the sedimentation of multiple sample on a single slide is difficult if not impossible to achieve.

A similar device to the Shandon-Elliott unit is described in an article entitled "A Device for Preparing Cell Spreads" by C. F. Dori et al., Immunology, 1965, 9, 403. Dori et al. note if the pressure on the slides (and filter paper) is insufficient, a majority of the cells are pulled out into the filter paper. Conversely, they note, too great a pressure prevents the preparations from drying in a short period of time (15 minutes). It is thus apparent that the devices of the prior art for preparing particle spreads on slides are not entirely satisfactory.

SUMMARY OF THE INVENTION

According to this invention a centrifuge rotor for depositing suspended particles of samples on deposition surfaces has an annular receptacle, with radially inner and outer walls, the outer wall having circumferentially located regions each adapted to receive one of the surfaces in vertical disposition, a plurality of removable chambers each adapted to hold one of the samples and being radially positionable in the receptacle between one of the surfaces and the inner wall, each chamber having an inlet orifice for introducing one of said samples into the chamber and an outlet orifice removably contacting one of the surfaces, and conduit means disposed in each chamber in the vicinity of the orifice for withdrawing fluid from the chamber and from the region of a corresponding surface in contact with the outlet orifice. With this arrangement, the centrifuge may be run for a sufficient period of time to permit the particles to pellet or sediment and be deposited on the surface. Then, the supernatant or fluid above the sedimented particles is withdrawn by applying a suitable vacuum to the conduit means. Once the supernatant is withdrawn, the centrifuge run may continue until the cells are dried. Alternatively, a staining dye may be introduced through the conduit means to stain the cells as desired. After staining, excess dye is removed in a manner similar to the excess fluid and the now stained cells again dried.

A gasket is positioned about each outlet orifice between the surface and the orifice. In a preferred embodiment each conduit means includes a tube extending radially through the chamber into a recess formed in the back wall of the chamber (adjacent the receptacle inner wall) and a corresponding fluid conduit means in the inner wall adapted to removably engage the tube. In this manner the fluid may be withdrawn from the chamber by applying a vacuum through a central rotating seal. The fluid conduit means is spring loaded to permit the chamber to be removed simply by withdrawing the fluid conduit means from the recess in the back wall of the chamber. A pivoted lever may be used to facilitate withdrawing the fluid conduit.

In alternative embodiments, the conduit means includes the tube, that extends radially inward from the outer orifice a pre-determined distance and then radially outward a distance greater than the predetermined distance. In this manner the centrifugal force will cause a fluid flow, once started, to exhaust the chamber of supernatant fluid by itself. The control over this flow may be enhanced by the use of an additional inlet tube extending radially into the chamber close to the surface for introducing fluid into the chamber until it is filled to a radial distance exceeding the pre-determined distance thus permitting a siphon type flow to occur.

With the device of this invention, relatively large cell populations may be deposited and dried on microscope slides for subsequent analysis. The device is easily used, cleanable and replaceable. Further, the cells may be deposited essentially "dry" by removing the fluid as occurs in the prior art devices using filter paper for this purpose. Multiple samples may be deposited on the same slide to build up cell populations.

BRIEF DESCRIPTION OF THE DRAWINGS

Further advantages and features of this invention will become apparent upon consideration of the following description wherein:

FIG. 1 is a partial plan view of a bowl-type centrifuge rotor constructed in accordance with this invention for depositing suspended particles on slides;

FIG. 2 is an elevation view partly in section of the rotor depicted in FIG. 1;

FIG. 3 is a partial cross sectional, elevation view of the rotor of FIG. 1 depicting a sample chamber in position engaging its corresponding slide;

FIG. 4 is a schematic representation of an alternative chamber that may be used to sediment samples;

FIG. 5 is a schematic representation of a chamber constructed in accordance with another embodiment of this invention; and FIG. 6 is a schematic representation of still another alternative chamber of this invention.

DESCRIPTION OF THE PREFERRED EMBODIMENT

There may be seen in FIGS. 1-3 a bowl-type rotor 10 having an otherwise conventional hub 12 (FIG. 3) adapted to seat on a conventional centrifuge drive spindle (not shown). The spindle is adapted to seat within the formed, tapered recess 14. The rotor 10 has an integrally formed base 16 and outer wall 18 and preferably is molded out of a suitable rigid material normally used for centrifuge rotors. Preferably the rigid material may be a suitable clear plastic such as a polycarbonate sold under the trade name "Lexan". Alternatively, some of the polyolefin resins or methacrylate resins may be used depending on the centrifugal force to which the rotor is to be subjected.

The base 16 is formed with an annular recess which defines an annular receptacle or trough 20. As will be described, the annular receptacle 20 is adapted to accommodate a plurality of removable sample chambers 22.

The annular receptacle 20 is interrupted by circumferentially spaced septa 24 formed integrally with the base and outer wall such that the regions between the septa defines cavities which are adapted to removably support the chambers 22 on either side as well as the back and front walls. At each septa, the height of the outside wall 18 is increased to provide a plurality of castellations 26 with the gap 28 between castellations being adapted to permit the insertion of one's fingers to grip a microscope slide or other planar deposition surface 30 (FIG. 3) on which particles or cells are to be deposited in accordance with this invention. To support the microscope slides 30, the inner surface of the outer wall 18 has a plurality of flat or planar portions 29 between each septa.

In similar manner, the back wall of each chamber 22 is supported by a removable annular support ring 34 which has a protuberance or key 36 on the bottom portion thereof adapted to fit into a locking groove 38 formed in the base 16 of the rotor 10. The radially outer surface 40 of the support ring 34 provides an inner support for the back wall of the chamber and has a corresponding flat or planar portion 31 within each cavity adapted to accommodate the various chambers as described.

The upper portion of the support ring 34 is formed to have radial flanges 45 spaced circumferentially at the location of each chamber, on which is a stud 47 on which a link 48 slides. There are bores 44 and corresponding counterbores 46 circumferentially located about the support ring 34 through each flange 45 to permit fluid communication with each of the chambers. The other end of the link engages a pivot stud 50 on a pivot arm 52. The lower portion of the pivot arm has a pivoted lock collar 54 adapted to engage a rigid tube 56, which may be formed of stainless steel or other suitable rigid, chemically inert material, to provide a fluid conduit as will be described. The tube 56 is adapted to slide within the bore 44 and counterbore 46. To afford engagement with the chamber 20, the tube 56 has an enlarged end portion 58 and the extreme end is rounded as at 60 with the end of the tube bore flared as at 62. A retaining collar 64 engages the tube 56 so as to prevent its outward movement beyond the counterbore. A compression spring 66 fitted about the tube and retained by a plate 68 urges the tube 56 outward through the support ring 34 to protrude into the annular cavity. The other end of the tube 56 is adapted to be connected such as by a flexible fluid coupling 69 to tube studs 70 which are friction fitted into a distributor 72 of conventional design.

The top portion of the distributor 72 accommodates a fixed inlet tube 74 which is introduced through a rotating seal 76 which is maintained in position by a plate 78 which is secured by screws 80. The screws 80 pass through the distributor 72 and engage the hub 12. This distributor 72 permits fluid to be introduced to or from the inlet tube 74, distributed through the several studs 70, and then through the various spring-loaded tubes 56 to the several chambers.

Each chamber 20 preferably may be formed of a clear plastic material of the same type as the rotor, is basically rectangular in shape, and is formed to hold the sample for sedimentation on a slide or deposition surface. Furthermore, each chamber has a vertical tapered bore 90 which forms an inlet and a horizontal, radially, outwardly disposed bore 92 which forms an outlet. The outlet bore 92 is counterbored as at 94 to facilitate the introduction of a gasket 96 which, when the chamber is in place, contacts the slide 30 to prevent leakage therebetween. The outer wall 18 has a flared bore 100 at each chamber location so that the deposition of cells or particles on the slides may be viewed. Finally, a tube or conduit 102 is placed with a radial orientation in each chamber with the outlet tube end approaching a point immediately contiguous the slide 30. The back or inner end of the conduit 102 passes through a shaped (rounded) recess 104 which is adapted to engage the rounded tip 60 of the spring-loaded tube 56. Vertical ridges (not shown) may be formed on the outer wall of each chamber so as to facilitate its fitting within the castellations 26 although these are not necessary.

In operation one simply needs to insert the sample chambers into the respective cavities in the annular receptacle. This is accomplished by depressing the pivot arm 52, thereby withdrawing the tube 56. Next the slide 30 or other deposition surface is positioned against the outside wall of the chamber 22 and the combination of the slide and chamber introduced into the annular receptacle 20 properly centered between the septa. The pivot arm is released such that tube 56 now springs forward and engages the recess for conduit 102 to complete the fluid circuit to the inlet tube 74. Desirably the chambers are filled in pairs disposed on opposite sides of the rotor to maintain balance if less than all chambers are used.

The sample may be introduced into the chamber inlet 90. Typically the sample may be blood and blood cell suspensions containing the blood cells which are desired to be deposited on the slide 30. The centrifuge is operated typically at several thousand revolutions per minute, although different speeds may be used depending on the results desired. Once the cells have become deposited on the slides, a vacuum is applied at the inlet tube 74 thereby to remove any supernatant (plasma in the case of blood) which is now virtually free of the cells. The centrifuge may be continuously operated during this time. Following removal of the supernatant, the spinning operation continues to dry the slide if desired. In any event following this the slides may now be removed and examined. Alternatively, dye may be introduced through the inlet tube 74 so as to provide appropriate staining for the deposited cells on the slides. In this event, the drying operation may be repeated following the withdrawal by vacuum of any excess dye. Alternatively, the supernatant may be removed quickly such that the cells are spun down almost dry.

The advantages of this invention aside from its simplicity are many. Essentially, the yield in cells deposited is quite high and the device is more reliable in affording good cell deposits than is provided or permitted by the prior art. Furthermore this approach facilitates drying and staining of the slide, if desired. Multiple samples may be sedimented on a single slide.

In alternative embodiments of the invention the design of the chamber may be modified to afford different ways of removing the excess fluid or supernatant. Thus, in FIG. 4 there is shown schematically an approach whereby the conduit 102, instead of being returned to the spring-loaded tube as described before, is simply brought back (radially inward) by the radial distance X and then returned (radially outward) to a point beyond the outer wall of the chamber such that once fluid fills the outlet portion of the chamber beyond the distance X, a fluid flow or siphon will be established which will be maintained until all the excess fluid is removed. Although shown only schematically, it is to be understood that the fluid connection to the tube may be made by a spring-loaded interconnector, of the type illustrated in FIG. 3, disposed in the outer wall of the rotor. Or, the outer wall and base of the rotor may be slotted to accommodate the exhaust conduit 102. In this instance the exhausted fluid will atomize or "aerosal" within the housing (not shown) for the rotor.

An alternative to this modification is shown in FIG. 5 in which an extra transport tube 120 is introduced with a deflector 122 at its outlet end so that fluid may be specifically introduced, from the upper portion 124 of the chamber, to fill the chamber with fluid to the distance X, following centrifugation and deposition of the slides, thereby to exhaust the chamber. The transport tube may be supplied from the distributor as in FIG. 1 using a spring-loaded contact, which is not shown for the sake of simplicity, in the same manner as shown in connection with FIGS. 1–3.

Still a further alternative embodiment of the invention is depicted in FIG. 6. In this instance, the exhaust tube is connected to a line 130 which provides a flow of fluid thereby to aspirate the fluid from the chamber. In FIG. 6, as was the case for FIGS. 4 and 5, this connection may be made to the chamber using a spring-loaded contact, if desired. The line 130 is formed in the base of the rotor and is supplied with fluid through the rotating seal illustrated in FIG. 1. In fact, if a double rotating seal is used, the fluid in line 130 may be returned through the rotating seal to an exhaust chamber not shown.

There has thus been described a relatively simple system for sedimenting cells or particles on slides. The yield is quite high and the device is relatively simple to operate.

We claim:

1. A centrifuge rotor for depositing suspended particles of a sample carried in a supernatant onto a deposition surface comprising:
   a region in said rotor adapted to receive said surface therein;
   a removable chamber adapted to hold said sample, said chamber being positionable in said region, said chamber having an inlet orifice for introducing said sample into said chamber and an outlet orifice contiguous to said surface through which the particles in said sample and the supernatant may pass radially outwardly of the rotor toward said surface; and,
   a conduit extending through a portion of said chamber for removing the supernatant from said surface in a radially inwardly direction of said rotor.

2. A centrifuge rotor of claim 1 wherein said conduit means extends through said chamber radially inwardly a predetermined distance and then radially outwardly a distance greater than said predetermined distance.

3. A centrifuge rotor of claim 2 further comprising an inlet tube extending radially into said chamber to a point contiguous said surface for introducing fluid into said chamber.

4. A centrifuge rotor of claim 1 wherein said conduit is connected to aspirating means for applying a vacuum to said conduit.

5. A centrifuge rotor of claim 1 further comprising means mounted on said rotor radially inwardly of said chamber and connectable to said conduit for applying a vacuum thereto.

6. A centrifuge rotor for depositing suspended particles of samples carried in a supernatant onto deposition surfaces comprising:
   an annular receptacle in said rotor, said receptacle having radially inner and outer walls, said outer wall having circumferentially located regions each adapted to receive one of said surfaces in vertical disposition;
   a plurality of removable chambers each adapted to hold one of said samples, each chamber being positionable between one of said surfaces and said inner wall, each chamber having an inlet orifice for introducing one of said samples and an outlet orifice through which the particles and the supernatant in that sample may pass radially outwardly of said rotor toward one of said surfaces; and
   a conduit extending through each said chamber from a point contiguous said chamber outlet orifice for withdrawing fluid from said chamber and from the corresponding one of said surfaces contiguous said chamber outlet orifice, said conduit extending radially inwardly through said chamber into a recess formed in said chamber adjacent said receptacle inner wall; and
   corresponding fluid conduit means in said inner wall adapted to removably engage said conduit to apply a vacuum thereto, thereby to withdraw the supernatant from each said chamber.

7. A centrifuge rotor of claim 6 wherein each said chamber has a gasket positioned about said outlet orifice between said surface and said chamber's orifice.

8. A centrifuge rotor of claim 6 wherein each said fluid conduit means is spring loaded.

9. A centrifuge rotor of claim 8 which includes a pivoted lever mounted on said rotor for withdrawing each said fluid conduit means from contacting said recess, thereby to permit removal of said chambers.

10. A centrifuge rotor of claim 9 which includes a rotating seal in said rotor for providing a continuous fluid communication path to said fluid conduit means.

11. A centrifuge rotor of claim 6 wherein said rotor has plural septa forming said regions, each of which supports a different one of said chambers.

* * * * *